United States Patent
Delpoux et al.

(10) Patent No.: US 10,935,493 B2
(45) Date of Patent: *Mar. 2, 2021

(54) OPTIMISED METHOD FOR DETECTING THE FORMATION GAS HYDRATES

(71) Applicant: IFP Energies nouvelles, Rueil-Malmaison (FR)

(72) Inventors: Olivier Delpoux, Voiron (FR); Didier Frot, Saint Germain en Laye (FR); Anne Sinquin, Bezons (FR); Corinne Sagnard, Blyes (FR); Veronique Lachet, Orsay (FR)

(73) Assignee: IFP ENERGIES NOUVELLES, Rueil-Malmaison (FR)

(*) Notice: Subject to any disclaimer, the term of this patent is extended or adjusted under 35 U.S.C. 154(b) by 31 days.

This patent is subject to a terminal disclaimer.

(21) Appl. No.: 16/470,681

(22) PCT Filed: Nov. 30, 2017

(86) PCT No.: PCT/EP2017/080968
§ 371 (c)(1),
(2) Date: Jun. 18, 2019

(87) PCT Pub. No.: WO2018/114267
PCT Pub. Date: Jun. 28, 2018

(65) Prior Publication Data
US 2020/0088644 A1    Mar. 19, 2020

(30) Foreign Application Priority Data
Dec. 21, 2016   (FR) .................................... 16/62.982

(51) Int. Cl.
*G01N 21/65*   (2006.01)
*G01N 33/22*   (2006.01)
*G01J 5/08*    (2006.01)

(52) U.S. Cl.
CPC .......... *G01N 21/65* (2013.01); *G01N 33/225* (2013.01); *G01J 5/0846* (2013.01); *G01N 2201/088* (2013.01)

(58) Field of Classification Search
None
See application file for complete search history.

(56) References Cited

U.S. PATENT DOCUMENTS

| 10,775,311 B2 * | 9/2020 | Delpoux ................ G01N 21/65 |
| 2011/0228265 A1 * | 9/2011 | Durickovic ........... G01N 21/65 |
| | | 356/301 |

FOREIGN PATENT DOCUMENTS

| FR | 2984504 A1 | 6/2013 |
| WO | 2010/043824 A1 | 4/2010 |

OTHER PUBLICATIONS

International Search Report for PCT/EP2017/080968, dated Jan. 17, 2019, and English translation submitted herewith (10 pages).

(Continued)

*Primary Examiner* — Shawn Decenzo
(74) *Attorney, Agent, or Firm* — Fitch, Even, Tabin & Flannery, L.L.P.

(57) ABSTRACT

The present invention relates to a method for detecting the presence of gas hydrates and/or ice in a medium. The method comprises at least the following steps:

measuring at least at one measurement point in said medium two characteristic values of Raman spectra corresponding to two distinct vibration modes of the OH bonds of water, and determining the ratio τ of said two characteristic values, determining the temperature T in said medium at said measurement point of said spectra, comparing ratio τ with a value $\tau_0$ corresponding to a predetermined threshold of formation of said crystals for said temperature T, and (Continued)

determining the presence or not of hydrate and/or ice crystals from said comparison.

9 Claims, 1 Drawing Sheet

(56) References Cited

OTHER PUBLICATIONS

Schicks J M et al: "Raman spectra of gas hydrates—differences and analogies to ice 1h and (gas saturated) water", Spectrochimica Acta. Part A: Molecular and Biomolecular Spectroscopy, Elsevier, Amsterdam, NL, vol. 61, No. 10, Aug. 1, 2005 (Aug. 1, 2005), pp. 2399-2403, XP027703263, ISSN: 1386-1425.
Chi Lo et al: "Investigations of surfactant effects on gas hydrate formation via infrared spectroscopy", Journal of Colloid and Interface Science, Academic Press, Inc, US, vol. 376, No. 1, Mar. 3, 2012 (Mar. 3, 2012), pp. 173-176, XP028410237, ISSN: 0021-9797.
Xu Xue et al: "Detection of water-ice phase transition based on Raman spectrum", Journal of Raman Spectroscopy, vol. 44, No. 7, Jul. 24, 2013 (Jul. 24, 2013), pp. 1045-1048, XP055367175, GB ISSN: 0377-0486.
Andreas Braeuer et al: "A Raman technique applicable for the analysis of the working principle of promoters and inhibitors of gas hydrate formation", Journal of Raman Spectroscopy, vol. 46, No. 11, Nov. 25, 2015 (Nov. 25, 2015), pp. 1145-1149, XP055366542, GB ISSN: 0377-0486.
Written Opinion of International Searching Authority for PCT/EP2017/080968.

* cited by examiner

OPTIMISED METHOD FOR DETECTING THE FORMATION GAS HYDRATES

CROSS-REFERENCE TO RELATED APPLICATIONS

This application is a U.S. national phase application filed under 35 U.S.C. § 371 of International Application No. PCT/EP2017/080968, filed Nov. 30, 2017, designating the United States, which claims priority from French Patent Application No.: 16/62.982, filed Dec. 21, 2016, the entire content of each of which are hereby incorporated herein by reference.

FIELD OF THE INVENTION

The present invention relates to the technical field of natural gas production and storage, and more generally to essentially gaseous fluids likely to form hydrate crystals or clathrates in a pipe.

The invention relates to an optimized method for detecting the presence or the propensity for formation of hydrates of a gas or hydrates of a gas mixture in an essentially gaseous fluid.

BACKGROUND OF THE INVENTION

Cells for studying the capacity of a system consisting of liquid and gas to form gas hydrates are known. In laboratory installations, pilot and/or industrial plants, gas hydrate formation is detected either by a temperature increase because crystallization is exothermic, or, when the working device is respectively closed or semi-closed (allowing the pressure to be maintained), by a pressure drop or by a sudden gas consumption. It is also possible to detect hydrate formation by visual examination. It should be emphasized that, in most of these methods, it is necessary to form (or to dissociate) a large number of hydrate crystals to obtain a significant result. In the case of gas systems with low water contents, equilibrium cells with water content measurement by gas chromatography or coulometry are used.

Gas hydrates are crystals comprised of a network of water molecules stabilized by hydrate formers (such as $CO_2$, $H_2S$, nitrogen, . . . ). Gas hydrates form under high pressure and low temperature conditions. If these crystals form, they grow, agglomerate and eventually clog pipes. Clogging remediation is long, difficult and dangerous. Currently, operators implement extensive and costly technical solutions to prevent formation of such crystals.

One object of the present invention is to provide a method enabling early detection and measurement of gas hydrate formation, thus allowing implementation of effective remediation techniques for hydrate formation.

Raman spectrometry is a non-destructive and non-invasive technique for studying molecular bond vibrations that is currently used for investigating the structure and the composition of natural or synthetic gas hydrates. Indeed, it is known that, in case of pure gas hydrates, Raman spectrometry allows to identify, through the vibration modes of the host molecules, the structure of the gas hydrate (of SI, SII or SH type) and to quantitatively determine the relative occupancies of the various cavity types of these different hydrate crystals. In the case of mixed hydrates (stabilized by a gas mixture), the technique allows to qualitatively identify the structure of the hydrate formed and the nature of the host molecules.

Raman spectrometry has already been used as a means of studying solid water formation.

The present invention is based on the use of Raman spectra in the vibration mode zone of the OH bonds of a water-containing medium likely to form solid crystals (such as ice and/or hydrates), with the combination of a temperature measurement. By limiting the use of Raman spectra in the vibration mode zone of OH bonds, the hydrate detection method is less long and less expensive than current methods: indeed, it is not necessary to sweep the whole spectrum.

SUMMARY OF THE INVENTION

The object of the present invention thus relates to a method for detecting the presence of gas hydrates and/or ice in a water-containing medium likely to form solid crystals, characterized in that it comprises at least the following steps:
measuring at least at one measurement point in said medium at least two characteristic values of Raman spectra corresponding to two distinct vibration modes of the OH bonds of water, and determining the ratio $\tau$ of said two characteristic values,
determining the temperature T in said medium at said measurement point of said spectra,
comparing ratio $\tau$ with a value $\tau_0$ corresponding to a predetermined threshold of formation of said crystals for said temperature T, and
determining the presence or not of hydrate and/or ice crystals from said comparison.

The two vibration modes can correspond to a wavenumber at $3160$ cm$^{-1}$±$40$ cm$^{-1}$, and to a wavenumber at $3400$ cm$^{-1}$±$150$ cm$^{-1}$.

The characteristic value can correspond to the intensity of said two modes on the spectra, or to a value directly related to the intensity, for example the integral of said spectrum centered on said vibration modes.

According to an embodiment of the invention, the temperature in the vicinity of the measurement point of said two characteristic values can be adjusted so as to anticipate the formation of solid crystals, hydrates for example.

According to an embodiment option, the presence or not of hydrate crystals can be deduced as a function of said comparison and as a function of the comparison between said measured temperature and the ice formation temperature under the measurement conditions.

Advantageously, the presence of hydrate crystals can be deduced if ratio $\tau$ is greater than a calibration value $\tau_0$ and if the measured temperature is higher than the ice formation temperature Tf under the measurement conditions.

According to an embodiment of the invention, in case of presence of hydrates, an anti-hydrate additive is injected into said medium.

BRIEF DESCRIPTION OF THE FIGURES

Other features and advantages of the present invention will be clear from reading the description hereafter of embodiments given by way of non-limitative examples, with reference to the accompanying figures wherein.

DETAILED DESCRIPTION OF THE INVENTION

Figure 1:
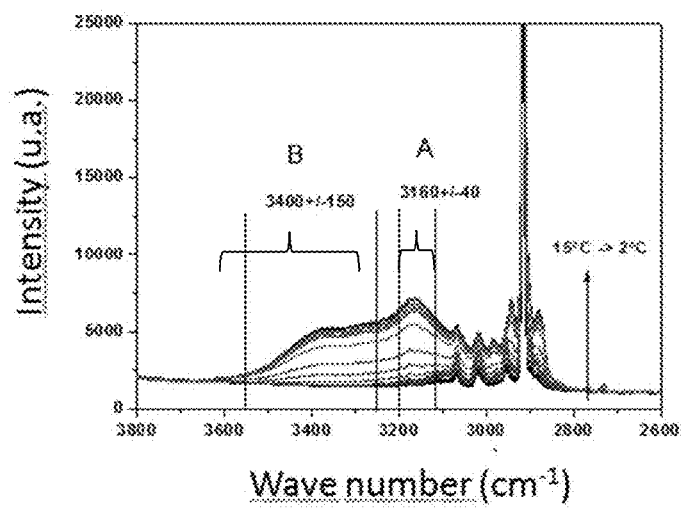
FIG. 1 shows Raman spectra as a function of the temperature of the medium considered.

The present invention relates to a method for detecting the appearance of hydrate crystals, and more generally of solid crystals in a water-containing medium, by coupling characteristic values obtained from Raman spectrometry in the spectral range of the vibration modes of OH bonds and from a temperature sensor. Solid crystals are understood to be gas hydrate crystals and/or ice crystals. Detection of the vibration modes of the OH bonds allows to qualify the OH bonds present in liquid water, in ice and/or in hydrates. It is thus possible to determine whether ice and/or hydrates have formed.

It is reminded that Raman spectrometry is an optical method of observing and characterizing the molecular composition and the external structure of a material. Raman spectrometry exploits the physical phenomenon according to which a medium slightly modifies the frequency of the light circulating therein. Raman spectroscopy consists in sending a monochromatic light onto the sample and in analyzing the scattered light. The information obtained by measuring and analyzing this shift makes it possible to trace certain properties of the medium, by spectroscopy.

The signal from the Raman spectrometer is transmitted to the medium by a probe known as Raman probe. The Raman probe also allows to lead the signal from the measurement point to the spectrometer. Advantageously, the Raman probe can be immersed in the water-containing medium. The Raman probe immersed in the water-containing medium can come in form of a cylindrical steel tube connected to two optical fibers, the "outward" fiber (or first fiber) leading the signal from the laser source to the measurement point and the "return" fiber (or second fiber) leading the Raman signal from the measurement point to the spectrometer.

The immersed end of the probe consists of a window, generally made of sapphire, allowing light rays to pass.

This end is directly immersed in the medium to be analyzed, thus enabling in-situ analysis. The immersed probe(s) can be arranged at different points of the unit, depending on the objective pursued.

According to an embodiment of the invention, the Raman spectrometer used can be a dispersive Raman spectrometer with an excitation laser wavelength below 785 nm (a frequency-doubled Nd-YAG for example ($\lambda$=532 nm)), a toric input mirror (improving image quality on the detector by correcting optical aberrations, in particular astigmatism) and a CCD detector. Selection of the laser and of the detector is conditioned by the search for optimum conditions in terms of signal-to-noise ratio in the spectral range of the vibration modes of OH bonds.

Near to the point of the unit where the Raman spectrum is measured, a temperature sensor (a thermocouple for example, or a third optical fiber allowing to offset the sensor, or any other temperature measuring means) can be installed so as to simultaneously have the Raman spectrum and the temperature of the sample zone. Thus, each measurement point of the Raman spectroscopy is associated with a temperature measurement in the vicinity of the measurement point, allowing to measure the temperature of the fluid at least in the vicinity of this measurement point.

Alternatively, the temperature can be known by any other means, for example measurement at another point, conditions imposed on the medium, etc.

Both data (Raman spectrum and temperature) can be sent to analysis means, notably computer means (a PC for example) controlling the analytical chain, for exploitation of these measurements.

A mathematical spectral decomposition method is then implemented in order to evaluate, after baseline subtraction (a method known to the person skilled in the art), a characteristic value for each of the following two vibration modes of the OH bonds (also referred to as water vibration modes):
  a first water vibration mode (referred to as mode A hereafter), such as that with a wavenumber at 3160 $cm^{-1} \pm 40\ cm^{-1}$, and
  a second water vibration mode (referred to as mode B hereafter), such as that with a wavenumber at 3400 $cm^{-1} \pm 150\ cm^{-1}$.

By limiting the use of Raman spectra in the OH bond vibration mode zone, the hydrate detection method becomes less long and less expensive than current methods: indeed, it is not necessary to sweep the whole spectrum.

A "characteristic value" is understood to be the intensity of the signal or a value directly related to the intensity, for example the area (obtained by integration of the spectrum on bands corresponding to the two water vibration modes).

The position of the bands corresponding to vibrations modes A and B can be given in wavenumber ($cm^{-1}$) or in wavelength (nm). It is reminded that the wavenumber is a quantity inversely proportional to the wavelength. This position of the bands is always given in relative terms (Raman shift) in relation to the position of the incident laser (the position of the bands expressed in wavelength depends on the wavelength of the incident laser of the Raman spectroscope).

Once the two characteristic values determined, a ratio $\tau$ of these two characteristic values is calculated. Preferably, the ratio corresponds to the ratio of the first water vibration mode (mode A) to the second water vibration mode (mode B).

Ratio $\tau$ is then compared with limit values $\tau_0$ previously determined by calibration in the medium considered. Limit values $\tau_0$ can depend on the medium, the temperature, the pressure, etc. Ratio $\tau_0$ can depend on the temperature, hence the interest of using a temperature measurement coupled with the Raman measurement. If $\tau > \tau_0$, then the system contains water in solid form (hydrates and/or ice). If $\tau < \tau_0$, then the system contains no water in solid form (hydrates and/or ice). Furthermore, when $\tau > \tau_0$, if temperature T measured in the vicinity of said measurement point is higher than ice formation temperature Tf under the measurement conditions, one can distinguish between a presence of ice or a presence of gas hydrates: if $\tau > \tau_0$ and T>Tf, then we can highlight the presence of gas hydrates.

Temperature Tf notably depends on the water-containing medium and on the pressure. In particular, temperature Tf can be high in the presence of an additive.

According to an example embodiment of the invention, ratio $\tau_0$ can range between 1 and 1.4 for the detection of hydrate formation in a methane-containing medium.

The calibration operation is possibly carried out at different temperatures, under conditions representative of industrial operations of the water-containing medium.

In short, from the calibration procedure, the on-line measurement of the Raman spectrum and temperature T in the vicinity of the measurement point, a limit value allowing to decide on the formation or not of water in solid form, notably in gas hydrate form, is determined.

According to an implementation of the invention, a device for cooling the medium at the measurement point can be added, so as to be able to control the temperature of the medium (by imposing a temperature range at the measurement point) in order to anticipate the formation of hydrates, or more generally of water in solid form.

According to an embodiment of the invention, if the formation of hydrates and/or of ice is detected at the measurement point after cooling the medium at the measurement point, it is possible to prevent hydrate formation in the medium by injecting an anti-hydrate additive into the water-containing medium. It is thus possible to anticipate hydrate prevention in the water-containing medium.

The method can comprise the following steps:
- sending at least to one point of the medium a light signal whose wavelength is below 785 nm,
- collecting the Raman spectrum at the point considered,
- processing the Raman spectrum according to the method described above (by measuring the characteristic values for the two OH bond vibration modes),
- obtaining at the end of this processing the value of intensity ratio $\tau$,
- measuring temperature T in the vicinity of the measurement point,
- comparing the value of ratio $\tau$ with a reference value $\tau_0$,
- according to the difference between measured value $\tau$ and reference value $\tau_0$, and according to the measured temperature, we decide on the presence or not of solid ice or hydrate crystals.

According to this information, it is possible to act on at least one action variable, for example temperature, pressure, additive injection or fluid flow rate, in order to prevent hydrate (or ice) formation in the water-containing medium.

In a variant, temperature T in the vicinity of the measurement point is controlled. A preliminary step of cooling said measurement point can be added. The method then allows to anticipate a hydrate formation temperature under real conditions.

EXAMPLE

Other features and advantages of the method according to the invention will be clear from reading the application example hereafter. In this example, the medium consists of methane in gas phase at a pressure of 70 bars and a small amount of water in an enclosure containing a temperature sensor and a ¼" Raman probe. The spectrometer used is a RXN2C marketed by the Kaiser company with an excitation length of 532 nm.

The Raman spectra illustrated in FIG. 1 were recorded upon cooling the enclosure between 15° C. and 2° C. Each curve corresponds to a temperature of the enclosure.

It can be seen in this figure that the major component is the methane in gas phase, with a main peak at 2917 $cm^{-1}$ corresponding to the symmetric stretching vibration of the CH bonds of methane. In the method provided, we do not seek to exploit the vibration modes of these CH bonds, but we rely on the analysis of the vibration modes of the OH bonds of water that can be seen in FIG. 1 in the 3100 $cm^{-1}$-3600 $cm^{-1}$ range approximately. In this zone, two water vibration modes can be seen: a first mode (denoted by A in FIG. 1) at 3160 $cm^{-1}$, and a second mode (denoted by B) at 3400 $cm^{-1}$. It is observed that the vibration range of the OH bonds undergoes changes during the temperature decrease. More precisely, it can be noted that the relative intensities of the two water vibration modes evolve as the temperature decreases, with a more significant intensity increase of mode A. This evolution is attributed to the formation of solid water in hydrate form when the temperature decreases from 15° C. to 2° C. (because the temperatures are higher than the melting point of ice).

Figure 2:
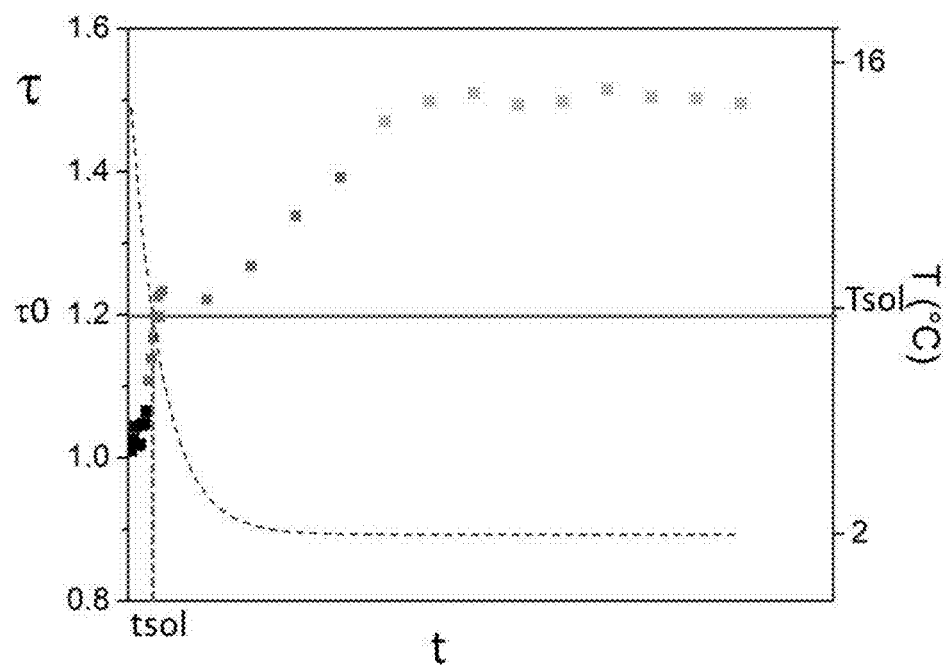
FIG. 2 shows the evolution of ratio $\tau$ of the Raman intensity of two different vibration modes of the OH bonds.

In this example, the intensities at wavenumbers 3173 $cm^{-1}$ and 3413 $cm^{-1}$ are measured. Ratio $\tau$ of the two intensities (I(3173)/I(3413)) is then calculated as a function of time (FIG. 2) or indifferently as a function of temperature since the temperature is lowered over time in this test. In FIG. 2, intensity ratio $\tau$ is represented by grey squares and the variation of temperature T in ° C. is illustrated by the dotted curve. The comparison of the values of ratio $\tau$, ranging here between about 1 and 1.5, with a reference value $\tau_0$ set here at 1.2 after prior calibration, allows to decide on the presence of water in solid form. In the region $\tau<\tau_0$, the system contains no water in solid form. In the region $\tau>\tau_0$, the system contains water in solid form. The time corresponding to the transition from one region to another, i.e. corresponding to the time when solid crystals form, is denoted by $t_{sol}$. The measurement of temperature T in the vicinity of the Raman spectra measurement point allows to convert this time $t_{sol}$ to a temperature $T_{sol}$ of solid particles appearance. In this example, the temperature ranges between 15° C. and 2° C., and temperature $T_{sol}$ of solid particles appearance is higher than the ice formation temperature, which additionally allows to conclude on the appearance of crystals of gas hydrate type rather than of ice type.

The invention claimed is:

1. A method for detecting the presence of gas hydrates and/or ice in a water-containing medium likely to form solid crystals, the method comprising:
   measuring, at least at one measurement point in the medium, two characteristic values of Raman spectra corresponding to two distinct vibration modes of the OH bonds of water, a first mode of the two distinct vibration modes having a wavenumber at 3160 $cm^{-1}\pm 40$ $cm^{-1}$ and a second mode of the two distinct vibration modes having a wavenumber at 3400 $cm^{-1}\pm 150$ $cm^{-1}$, and determining a ratio $\tau$ of the two characteristic values,
   determining a temperature T in the medium at the measurement point of the two characteristic values of Raman spectra,
   comparing the ratio $\tau$ with a value $\tau_0$ corresponding to a predetermined threshold of formation of the crystals for the temperature T,
   determining the presence or not of hydrate and/or ice crystals from the comparison of the ratio $\tau$ with the value $\tau_0$, and
   distinguishing between the presence of gas hydrates and ice by comparing the temperature T in the medium at the measurement point with an ice formation temperature.

2. The method as claimed in claim 1, wherein the two characteristic values of Raman spectra correspond to intensities of the two vibration modes, or to values directly related to the intensities of the two vibration modes.

3. The method as claimed in claim 1, further comprising varying the temperature in the vicinity of the measurement point of the two characteristic values of Raman spectra so as to anticipate the formation of solid crystals.

4. The method as claimed in claim 1, wherein the presence of hydrate crystals is deduced if the ratio $\tau$ is greater than a calibration value $\tau_0$ and if the temperature T in the medium at the measurement point is higher than an ice formation temperature Tf under measurement conditions.

5. The method as claimed in claim 4 wherein, in case of presence of hydrates, an anti-hydrate additive is injected into the medium.

6. The method as claimed in claim 1, wherein the two characteristic values of Raman spectra correspond to integrals of the Raman spectra centered on the vibration modes.

7. The method as claimed in claim 1, further comprising varying the temperature in the vicinity of the measurement point of the two characteristic values of Raman spectra so as to anticipate the formation of hydrates.

8. The method as claimed in claim 1, further comprising cooling the medium in the vicinity of the measurement point to anticipate formation of hydrates and/or ice.

9. The method of claim 8, further comprising detecting the presence of hydrates and/or ice at the measurement point after cooling the medium in the vicinity of the measurement point, and injecting an anti-hydrate additive into the water-containing medium when the presence hydrates and/or ice is detected.

* * * * *